United States Patent
Farieta et al.

(10) Patent No.: US 8,276,583 B2
(45) Date of Patent: Oct. 2, 2012

(54) DEVICE FOR DELIVERING MEDICAMENT

(75) Inventors: Antonio Farieta, Vallentuna (SE);
Victor Kronestedt, Stockholm (SE)

(73) Assignee: SHL Group AB, Nacka Strand (SE)

( * ) Notice: Subject to any disclaimer, the term of this patent is extended or adjusted under 35 U.S.C. 154(b) by 653 days.

(21) Appl. No.: 12/516,933

(22) PCT Filed: Jan. 8, 2008

(86) PCT No.: PCT/EP2008/050144
§ 371 (c)(1),
(2), (4) Date: Sep. 7, 2009

(87) PCT Pub. No.: WO2008/087071
PCT Pub. Date: Jul. 24, 2008

(65) Prior Publication Data
US 2010/0065049 A1    Mar. 18, 2010

Related U.S. Application Data

(60) Provisional application No. 60/885,292, filed on Jan. 17, 2007.

(30) Foreign Application Priority Data

Jan. 17, 2007 (SE) .................................. 0700107

(51) Int. Cl.
*A61M 5/31* (2006.01)
*A61F 9/00* (2006.01)
(52) U.S. Cl. .................... 128/203.15; 604/311
(58) Field of Classification Search ............ 128/203.15; 604/298, 311, 82
See application file for complete search history.

(56) References Cited

U.S. PATENT DOCUMENTS

| 4,973,318 | A | 11/1990 | Holm et al. |
| 5,514,097 | A | 5/1996 | Knauer |
| 6,319,225 | B1 | 11/2001 | Sugita et al. |
| 6,562,006 | B1 | 5/2003 | Hjertman et al. |
| 6,893,420 | B2 | 5/2005 | Arnisolle |
| 7,341,571 | B1 * | 3/2008 | Harris et al. ............... 604/96.01 |
| 7,427,275 | B2 | 9/2008 | DeRuntz et al. |

(Continued)

FOREIGN PATENT DOCUMENTS
EP    1365823 B1    5/2007
(Continued)

OTHER PUBLICATIONS

EPO, Intl Search Report in PCT/EP2008/050144, May 7, 2008.

(Continued)

*Primary Examiner* — Stephen Crow
(74) *Attorney, Agent, or Firm* — Potomac Patent Group PLLC (57) ABSTRACT

The present invention relates to a device for delivery of medicament comprising a main housing; a container arranged in said housing and arranged to be connected to a medicament delivery member, wherein said container includes at least two chambers and at least one longitudinally movable plunger and wherein at least one chamber contains a medicament agent; a pre-treating arrangement acting on said container; drive force means acting on a longitudinally movable plunger rod capable of exerting a force on said container; and activating delivery means acting a said drive force means for delivering medicament via said medicament delivery member characterised in that said pre-treating arrangement comprises clickable means for manually and delay intermittently mixing said medicament agent and for manually priming said container.

15 Claims, 4 Drawing Sheets

U.S. PATENT DOCUMENTS

| | | |
|---|---|---|
| 7,704,237 B2 | 4/2010 | Fisher et al. |
| 2005/0049551 A1 | 3/2005 | Kirchhofer |
| 2007/0142789 A1 | 6/2007 | Fisher et al. |
| 2008/0027397 A1 | 1/2008 | DeRuntz et al. |
| 2010/0065049 A1 | 3/2010 | Farieta et al. |
| 2011/0082420 A1 | 4/2011 | Brunnberg et al. |

FOREIGN PATENT DOCUMENTS

| | | |
|---|---|---|
| WO | 01/30425 A1 | 5/2001 |
| WO | 02/098479 A2 | 12/2002 |
| WO | 2006/080893 A1 | 8/2006 |
| WO | 2008/087071 A1 | 7/2008 |
| WO | 2009/147112 A1 | 12/2009 |

OTHER PUBLICATIONS

EPO, Written Opinion in PCT/EP2008/050144, May 7, 2008.

* cited by examiner

DEVICE FOR DELIVERING MEDICAMENT

TECHNICAL FIELD

The present invention relates to a device for delivering medicament to a patient and in particular in connection with containers containing medicament that needs to be pre-treated, e.g. correct mixed and primed, before the delivery of a dose of medicament to a patient.

BACKGROUND ART

Generally, there are a type of medicaments that can be stored for a long time and that are filled in containers as e.g. cartridges, syringes, ampoules, canisters or the like, containing a ready-to-use medicament in liquid state. There are also other type of medicaments that are a mixture of a medicament agent (e.g. lyophilized, powdered or concentrated liquid) and a diluent (e.g. water, dextrox solution or saline solution), wherein these type of medicaments can not be pre-mixed and stored for a long time because the medicament agent is unstable and can be degraded and loses its effect quickly. Hence, a user, e.g. a patient himself/herself, a physician, a nurse, hospital personnel or trained persons, has/have to perform the mixing within a limited time period prior to the delivery of a dose of medicament to a patient. Further, some medicament agents are subject to meet significant chemical changes while mixing. Such sensitive medicament agents require a particular treatment so that, when mixing said medicament agents with a diluent, unreasonable mixing force will degrade said medicament agents.

In order to facilitate the mixing, a number of containers for mixing have been developed comprising at least two chambers, a multi-chamber container, one chamber containing the medicament agent and the other chamber containing the diluent. Said chambers are sealed off with plungers in order that the medicament agents do not become degraded. When the medicament agent is to be mixed, e.g. passages are opened between the chambers, usually by depressing a rear plunger and in turn a divider plunger of the container somewhat. The passages allow the mixing of the medicament agent and the diluent and the medicament is ready for delivery.

Multi-chamber containers usually contain a lot of air/gas, especially when the medicament agent is in powder form, which air/gas is present when the medicament agent and the diluent are mixed. This entrapped air/gas is often desirable to get removed, priming, before delivery.

The above mentioned requirements can be achieved by simple medicament delivery devices, such as a common hypodermic syringe, but the procedure is of course rather awkward, in particular for persons not used to handle these devices. In order to facilitate for the patient themselves to administer the medicament with a predetermined dose in an easy, safe and reliable way and also to facilitate the administration of medicaments for hospital personnel in the same facilitated way, a number of automatic and semi-automatic devices have been developed in combination with these multiple-chamber solutions for obtaining a mixing before delivery.

A self-injection device arranged with a dual-chamber container, wherein both the mixing and the injection are done automatically by mechanical means, as springs and other means, is disclosed in U.S. Pat. No. 4,755,169.

A similar solution is disclosed in U.S. Pat. No. 6,793,646 wherein the mixing of a dual-chamber cartridge is done is done automatically by springs upon activation of the device and the injection is done by manually applying a force to a plunger rod forwardly.

A drawback with these devices is that the mixing force, to which medicament agents are subject to, is too high at the beginning due to Hookes law. Hence, the medicament agents can be degraded. Further, such devices can be primed holding them at different positions, which do not ensure that the air or gas entrapped in the container is expelled.

Another solution is disclosed in WO 2004004809, wherein both the mixing and the injection are done automatically by electronics controlled means. A drawback with this device is that the electronics are dependent on batteries and is very sensitive to noise, moisture, water, etc.; which can result in malfunctions. Even more the manufacture of these devices is more expensive than the manufacture of mechanical devices.

In U.S. Pat. No. 6,893,420 is disclosed a self-injection device arranged with a dual-chamber body. The penetration and injection is done automatically upon activation of the device and the mixing is done manually by a screw-tightening operation of a rear cap, whereby a plunger rod applies a force on a plunger inside the dual-chamber body such that a mixing is obtained. A drawback with this device is that users having impaired manual dexterity have difficulties in handling such a device.

Another similar solution is disclosed in U.S. Pat. No. 6,319,225 where the mixing of a dual-chamber ampoule is done by manually. The device is set to be vertical on a flat plane and then a downward press on its front case causes a relative upward movement of its plunger rod pressing a plunger of the ampoule with eye observation on actions inside the ampoule, such that a mixing is obtained. Though in U.S. Pat. No. 6,319,225 is disclosed that the best suitable process for mixing a medicament agent with a diluent, is by performing manual control of the diluent flow with adequate slowness which will be monitored by eye observation.

A drawback with the above mentioned devices is that the mixing force, to which medicament agents are subject to, can be high if the user is stressed and wants to use the device as soon as possible or. Hence, the medicament agents can be degraded. Further, the device disclosed in U.S. Pat. No. 6,893, 420 can be primed holding it at different positions, which does not ensure that the air or gas entrapped in the container is expelled.

Heretofore, a number of devices have been disclosed for pre-treating, e.g. mixing a medicament agent and a diluent and priming, multi-chambered containers before the delivery of a dose of medicament to a patient; but such devices admit of further improvements in view of pre-treating multi-chambered containers for preventing a too high mixing force degrading the medicament agents and priming in a correct and safe way.

BRIEF DESCRIPTION OF THE INVENTION

The aim of the present invention is to provide a medicament delivery device which improves the pre-treating e.g. correct mixing and priming, of multi-chamber containers before the delivery of a dose of medicament to a patient.

This aim is solved by the present invention characterised by claim 1. Additional advantageous developments of the present invention are characterised by the dependent claims.

According to one major aspect of the invention it is characterised by a device for delivery of medicament comprising a main housing; a multi-chamber container comprising a first chamber containing a diluent, a second chamber containing a medicament agent, a bypass channel, an outlet provided with means to be connected to a medicament delivery member and at least one longitudinally movable plunger; a pre-treating arrangement acting on at least one longitudinally movable plunger for mixing said medicament agent with said diluent and obtaining a mixed medicament; drive force means acting on a longitudinally movable plunger rod capable of exerting a force on said container for delivering the mixed medicament; and activating delivery means acting a said drive force means for initiating the delivering of medicament via said medicament delivery member wherein said pre-treating arrangement comprises clickable means resiliently and operably connected to a longitudinally movable second rod which is partially and slidable arranged inside the longitudinally movable plunger rod, such that the clickable means are adapted to be manually and intermittently activated for stepwise pushing the second rod inside said container and thereby mixing said medicament agent with said diluent.

According to another aspect of the invention, said clickable means are arranged and designed with delay means arranged around the clickable means for delaying the intermittently pushing of said second rod.

According to a further aspect of the invention, said pre-treating arrangement further comprises blocking means for permitting activation of said clickable means only when the device is substantially vertical with the medicament delivery member into a specific direction.

Yet another aspect with the present invention is that the device further comprises dose setting means arranged and designed to interact with the drive force means for adjusting a predetermined dose to be delivered.

According to another aspect of the invention, said activating delivery means are arranged and capable of extending around the medicament delivery member upon withdrawal of the device from the delivery site.

The advantages with the present invention are several compared to the state of the art. Because the device is capable of pre-treating a multi-chamber container by manually and delay intermittently mixing and priming said container, the diluent flows with adequate slowness inside the container, avoiding the degradation of the medicament agents. Further, because the device is only capable of pre-treating a multi-chamber container when the device is held substantially vertical, the liquid flow disturbance is avoided and the air or gas is removed after mixing and before delivery is correct controlled and reliable expelled. Moreover, if a user continues pre-treating the container even when the container has been primed, which is the last step of the pre-treating; it will not cause any impact on the pre-treating arrangement since the clicking means has been completely inactivated after said last step.

Regarding dose delivery, in contrast also to conventional devices where it could be difficult to deliver the proper, required dose, the device of the present invention is very easy to handle due to the dose adjusting capabilities presented. The patient merely sets the device to deliver the proper dose. It is of course possible with the present device to have a fixed dose that cannot be altered, which may be advantageous if for example children are to use it, or if it is desired to have a very easy-to-use functionality.

When used as an injector, the device preferably is provided with a needle shield that is capable of covering the needle after use, which needle shield is locked in that position. This prevents accidental needle-sticks on contaminated needles from occurring.

These and other aspects of and advantages with the present invention will become apparent from the following detailed description and from the accompanying drawings.

BRIEF DESCRIPTION OF THE DRAWINGS

In the detailed description of non-limiting examples of the invention reference will be made to the accompanying drawings, of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 1:
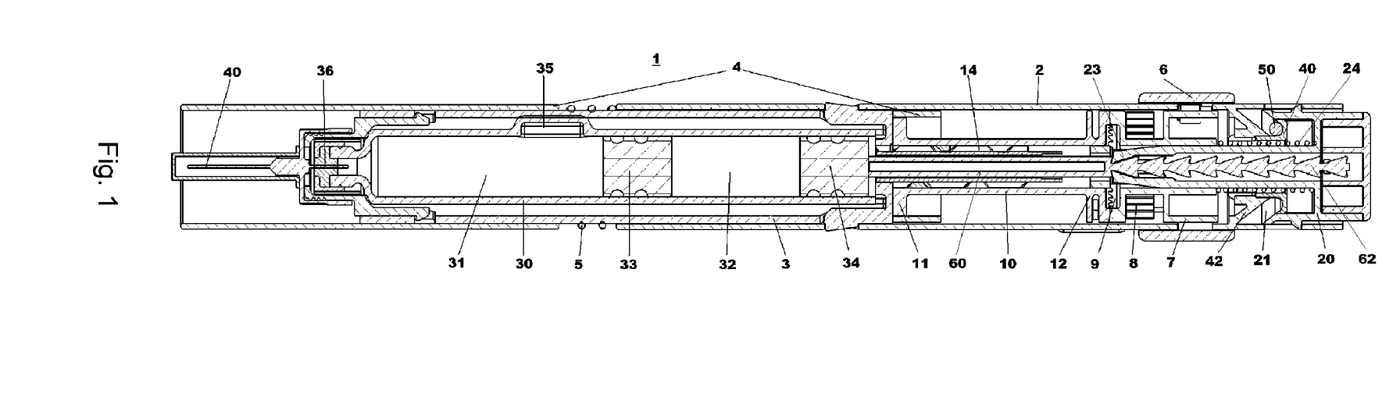
FIG. 1 is a longitudinal cross-sectional view of a preferred embodiment according to the invention in a state when it is delivered to the user.

As seen in FIG. 1 the delivery device 1 comprises in its distal end a main tubular housing 2 and in its proximal end a container housing 3 comprising a container 30. The container 30 is a multi-chamber container comprising two chambers of a proximal space 31, a distal space 32, a longitudinally movable middle plunger 33, a longitudinally movable distal plunger 34, a bypass channel 35 and an oulet 36 through which a mixed liquid medicament can be delivered. The proximal space being sealed with the middle plunger 33 comprises a medicament agent and the distal space being sealed with the distal plunger 34 comprises a diluent, wherein a displacement of the plungers causes the mixing of the medicament agent with the diluent forming the mixed liquid medicament to be delivered through the outlet. The outlet is provided with means in order to be connected to a suitable medicament delivery member 70. The medicament delivery member is preferably a mouth or nasal piece, which the patient puts in his mouth or nose, respectively, whereby a metered dose of medicament is inhaled by the patient. The medicament delivery member can also be a member that introduces the liquid medicament to the eye of the patient, such as a suitable nozzle that sprays the medicament to the eye, or a member that introduces the medicament to the eye in the form of droplets. Naturally, a nozzle as a medicament delivery member can also be used in order to spray the medicament onto the skin of the patient. The medicament delivery member can also be a needle for the injection of a liquid medicament into the body of the patient, wherein the medicament can have a low as well a high viscosity.

The container housing is surrounded by a tubular delivery member shield 4, wherein the proximal end of said delivery member shield extends beyond the proximal ends of the container housing 3 in order to protect the medicament delivery member 70, as seen in FIG. 1. The delivery member shield is further in its distal end provided with a helical delivery member shield spring 5, wherein said spring 5 is comprised between the delivery member shield 4 and the main tubular housing 2, as seen in FIG. 1.

As seen in FIG. 1, the delivery device 1 comprises further in its distal end, a dose setting turning member 6 connected to an energy accumulating member housing 7. The turning member 6 is further provided with a suitable dose indicating means (not shown), the function of which is to point out the set dose to be delivered. The energy accumulating member housing 7 is in its proximal end adapted to house an energy accumulating member 8 e.g. a flat spiral spring, wherein said flat spiral spring is provided winded in layers around the housing member. The energy accumulating member is in its inner end provided with suitable inner holding means (not shown) in order to be attached to the housing 7 and at its outer end provided with suitable outer holding means (not shown) in order to be connected to the main tubular housing 2. The energy accumulating member housing 7 is further in its distal end provided with a crown 9 provided with a number of equally distributed bevelled protrusions.

A seen in FIG. 1, the delivery device 1 comprises further in its distal end, a rotatable coupling member 10. Said rotatable coupling member 10 is in its distal end provided with a coupling crown 12 which is provided with a number of equally distributed beveled teeth adapted to be in contact with the protrusions of the crown 9. The rotatable coupling member 10 is further in its proximal end provided with a plunger rod driving member 11 provided with outwardly protruding flanges. The flanges are adapted to engage at least one ledge (not shown) arranged at the distal end on the interior the delivery member shield 4, such that the ledge(s) is/are provided in between two protruding flanges holding the rotatable coupling member 10 in a non-rotating state. Further, the coupling member 10 is adapted to be screw threaded on a longitudinally movable threaded plunger rod 14 which runs in the interior of the device along the longitudinal axis of said device. The interior of the rotatable coupling member 10 is thus provided with grooves of a predetermined pitch, i.e. a predetermined screw pitch, which corresponds to the thread of the plunger rod 14.

Thus, the device comprises drive force means (7, 8, 10) acting on a longitudinally movable plunger rod (14) capable of exerting a force on said container; and activating delivery means (4, 5) acting a said drive force means for delivering medicament via said medicament delivery member.

As seen in FIG. 1, the delivery device 1 comprises further in its distal end a pre-treating arrangement comprising clickable means resiliently and operably connected to a longitudinally movable second rod (60) which is partially arranged inside the longitudinally movable plunger rod (14), such that the clickable means are adapted to be manually and intermittently activated for stepwise pushing the second rod (60) inside said container and thereby mixing said medicament agent with said diluent.

Further, said clickable means comprises a sleeve 20, hereafter called pre-treating sleeve and a resilient means (24), wherein the pre-treating sleeve is adapted to be manually activated from a non-depressed position to a depressed position against a counteracting force from the resilient means; such that when the pre-treating sleeve is activated from the non-depressed position to the depressed position, the second rod is pushed one step inside the container and the pre-treating sleeve is restored to its non-depressed position for a further activation.

Moreover, said pre-treating arrangement comprises blocking means for permitting activation of said clickable means only when the device is substantially vertical with the medicament delivery member into a specific direction. Further, said blocking means comprises a cylindrical sleeve 40, a cylindrical wall 42 on the inner surface of the main tubular housing and obstruction means 50, wherein the inner surfaces of said blocking means are arranged and designed to interact with the clickable means.

Figure 2:
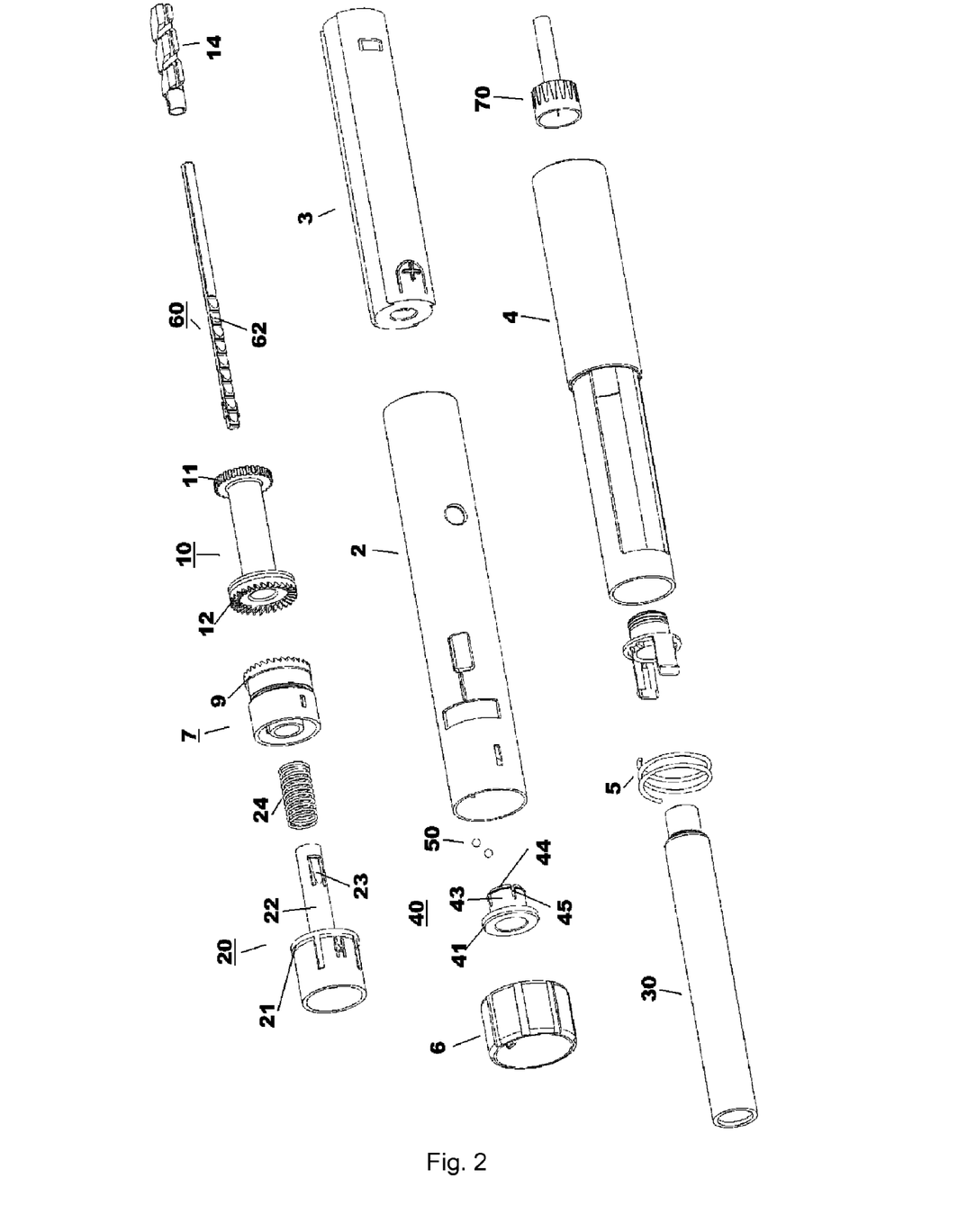
FIG. 2 is an exploded view of the device of FIG. 1.

Said pre-treating sleeve is slidable arranged inside the main tubular housing 2, wherein a distal part of said priming sleeve protrudes somewhat outside the main tubular housing 2. The distal part of the pre-treating sleeve is arranged with a circumferential ledge 21, where the inner surface of the ledge 21 slopes somewhat towards the centre of the sleeve, see FIG. 2. The inner diameter of the ledge 21 substantially corresponds to the diameter of an annular ledge 41 on the distal end of the cylindrical sleeve 40, see FIG. 2. In that area the cylindrical wall 42 on the inner surface of the main tubular housing, is arranged; wherein said cylindrical wall 42 has the same slope as the inner surface of the ledge 21 and wherein said wall 42 has also a central tubular passage, see FIG. 1. Further, as seen in FIG. 2, the cylindrical sleeve 40 comprises a tubular part 43 having radially extending flanges 44 and indentation 45. Said tubular part 43 extends longitudinally through the central tubular passage of said wall 42, wherein said radially extending flanges 44 and indentations 45 are intended to co-act with a set ledges (not shown) of the wall 42. Further, the annular ledge 41 on the proximal end of a cylindrical sleeve 40 comprises a bowl-shaped inner surface. A delay means (not shown) as e.g. friction means arranged around the circumferential surface of the pre-treating sleeve at its distal end or spring delay means arranged and designed to interact with said compression spring.

Said obstruction means 50 as e.g. a ball, a sort of pendulum, tilt members or the like; placed in the space defined by the annular ledge 41 of the cylindrical sleeve 40, the sloping ledge 21 of the pre-treating sleeve 20 and the cylindrical wall 42. Further, as seen in FIG. 2, the pre-treating sleeve 20 comprises a tubular member 22, which extends out of the pre-treating sleeve 20 towards the proximal part of the device, wherein said tubular member 22 is provided with inwardly flexible tongues 23. Said resilient means24 is arranged between an end wall inside the pre-treating sleeve 20 and an end portion of the energy accumulating member housing 7, surrounding the tubular member 22 of the pre-treating sleeve 20.

The threaded plunger rod 14 is further provided as a hollow member wherein said longitudinally movable second rod 60 can be urged inside. Said second rod 60 can be a hollow member or a solid member. The longitudinally movable second rod 60 is designed and arranged with a ratchet 62 having a predetermined number of steps, wherein said steps are teeth with saw-toothed shape. Moreover, said ratchet is in contact with the inwardly flexible tongues 23 of the pre-treating sleeve 20. Further, the proximal end of said second rod 60 is in contact with the longitudinally movable distal plunger 34. Moreover, said second rod 60 and said threaded plunger rod 14 are provided with means (not shown) that prevents said second rod 60 from moving along its longitudinal axis towards the distal end of the device and/or from rotating after said second rod have been urged totally inside said threaded plunger rod 14.

Thus, the clickable means is arranged and designed to intermittently push/click said second rod (60) inside the plunger rod (14) and to exert a force on said container for manually pre-treating said container.

The device is intended to function as follows. When the device is to be used a front protection cap (not shown) is removed from the medicament delivery member 70. First the container has to be pre-treated e.g. mixing and priming, see FIG. 1. In order to ascertain that liquid flow disturbance is avoided and that the air/gas is removed before delivery, the device has to be held substantially vertical with the medicament delivery member 70 pointing upwards.

The present invention ensures that the pre-treating can only take place when the device is in that position, due to the mechanical pre-treating means. When the device is held substantially vertical, the gravitation and the sloping surfaces of the pre-treating sleeve 20 and of the wall 42 ensure that the obstruction means 50 is not longer blocking the pre-treating sleeve to be urged towards the proximal end of the device. Thus, in this position it is possible to hold the device on its main tubular housing 2 placing the flat external surface of the pre-treating sleeve 20 on a flat plane, e.g. a table, to manually push/click the pre-treating sleeve 20 towards the proximal end of the device against a counteracting force from the resilient means 24. The movement of the pre-treating sleeve 20 causes the inwardly flexible tongues 23 that are resting on the ratchet 62 of the second rod 60 to drive said second rod stepwise a predetermined distance towards the proximal end of the device. Since the proximal end of said second rod is in contact with the longitudinally movable distal plunger 34, said plunger 34 moves also one step inside the container towards the proximal end of the device, allowing the diluent to flow through the bypass channel into the chamber containing the medicament agent and thereby initiating the mixing of the medicament agent with the diluent. The movement of the second rod is stopped when the circumferential ledge 21 of the pre-treating sleeve 20 comes in contact with the cylindrical wall 42 of the main tubular housing 2. When the device raises up from the flat plane, the pre-treating sleeve 20 releases back to its original position with a predetermined delay due to the delay means. Further, when said pre-treating sleeve releases back, the inwardly flexible tongues 23 slide over one step of the ratchet 62 and rest on the second step of the ratchet. The mixing can continue by clicking the pre-treating sleeve 20 against the flat plane a predetermined number of times which is equal to the number of steps of the ratchet. The last clicking is intended to be the priming of the container and the pre-treating is accomplished in a safe, controlled and reliable way. Because the device is in the substantially vertical position, it is assured that the air/gas entrained in the container is removed before delivery. This pre-treating is done in a controlled way since the releasing of the pre-treating sleeve is done is several steps and/or comprises a delay and thus the user can not click the device quickly when he/she feels stressed. Moreover, if the user continues clicking even when the container has been primed at the last step of the pre-treating, it will not cause any impact on the pre-treating since the second plunger rod has come out of contact with pre-treating sleeve and has been urged totally inside the plunger rod 14.

The resilient means 24 further has the function of reducing the risk of jamming the obstruction means 50 when the pre-treating sleeve is pushed/clicked towards the distal end of the device.

Figure 3:
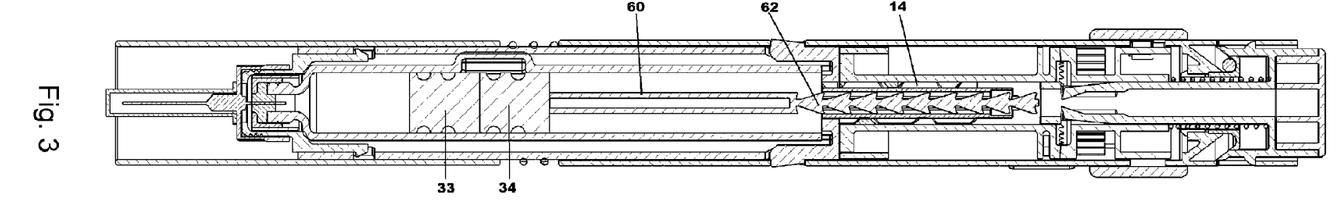
FIG. 3 is a longitudinal cross-sectional view corresponding to FIG. 1 in a state where a pre-treating has been performed.

When the pre-treating is completed, as seen in FIG. 3, the device is ready for a dose setting. The user first turns the dose setting turning member 6 to a certain prescribed dose, which preferably is shown by indications on the dose setting turning member. By turning the dose setting turning member 6, the housing 7 rotates as well, whereupon the protrusions of the crown 9 slide over the bevelled teeth of the coupling crown 12. Each time a protrusion slides over a tooth, the dose is increased by one step and the increase of the dose with one step corresponds to a clock-wise rotation of the turning member 6 with a predetermined number of degrees. Each time the housing 7 is rotated by one step, the energy accumulating member 8, winds up and accumulates energy that corresponds to the rotation of the dose setting turning member 6 the number of degrees that corresponds to one clock-wise step turn.

It is also possible to provide the device with means (not shown) that sets a certain dose as a default dose value, for instance by providing the exterior surface of the outer cover with a stopper means at the numerical indicator corresponding to the default dose value, which stopper means will prevent the user to rotate the dose setting turning member 6 further than the number of degrees corresponding to the default dose value.

If the delivery device needs to be reset, for instance if the user by mistake sets a too high dose, this is accomplished by pulling the dose setting turning member 6 towards the distal end of the device, such that the protrusions of the crown 9 will be brought out of engagement from the bevelled teeth of the coupling crown 12, whereby the dose setting turning member 6 can be rotated back.

When the pre-treating and dose setting are completed the device is ready for a delivery. This is accomplished by pushing the delivery member shield 4 towards the distal end of the delivery device, preferably by pushing the proximal end of the delivery member shield against the medicament delivery site. When the delivery member shield moves towards the distal end of the delivery device, the ledges arranged at the distal end on the interior the delivery member shield 4 comes out of engagement with the flanges of the plunger rod driving member 11, which will set the rotatable coupling member 10 and the housing 7 in a rotatable state due to the energy accumulated in the energy accumulating member 8.

Figure 4:
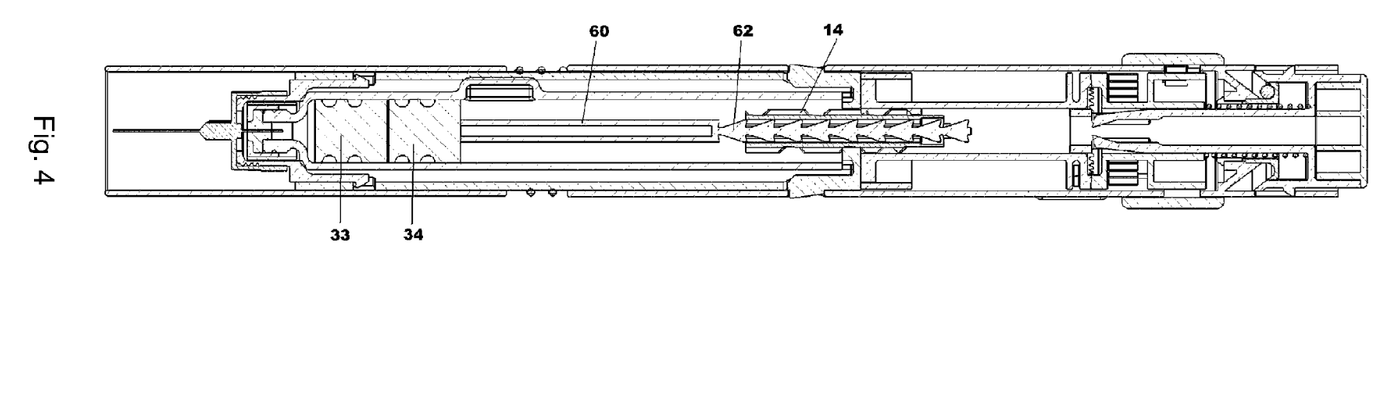
FIG. 4 is a longitudinal cross-sectional view corresponding to FIG. 1 in a state where a dose of medicament has been delivered to a patient.

The plunger rod 14 can be configured in a plunger-rod-non-rotating-state-configuration or in a plunger-rod-rotating-state-configuration. The rotation of the rotatable coupling member 10 will urge the plunger rod along the longitudinal axis of the rod towards the proximal end of the device a predetermined distance into the container 30. Since the proximal end of the second plunger rod 60 inside the threaded plunger rod 14 in any configuration is in contact with the plunger 34 provided inside the container 30, said plunger will move a predetermined distance towards the proximal end of the container and deliver the set volume dose of the mixed medicament. The device is designed in accordance with the container so that the movement of the plunger the predetermined distance towards the proximal end of the container will correspond to the delivery of the dose set. The housing 7 and the dose setting turning member 6 will thus rotate back to its original position extending around the medicament delivery member when the dose is delivered. When the dose has been delivered, as seen in FIG. 4, the user releases the delivery member shield 4, by simply removing the device from the delivery site, whereupon the delivery member shield will move back towards the proximal end of the delivery device by means of the spring force accumulated in the delivery member shield spring 5 when the delivery member shield was pressed towards the distal end of the device. The ledges arranged at the distal end on the interior the delivery member shield 4 will once again engage the flanges of the plunger rod driving member 11 and the plunger rod 14 will stay at its current position, in contact with the plunger 34, and the delivery device is ready to be used again.

The user of the delivery device can also release the delivery member shield during medicament delivery and hence set the delivery device in a medicament non-delivery state before the set dose has been delivered. The user can then once again push the delivery member shield towards the distal end of the device, whereby the set dose continues to be delivered. The procedure above can be repeated an optional number of times until the entire set dose has been delivered. This procedure is for instance suitable when a predetermined dose of medicament is to be delivered to a patient at multiple delivery sites, whereby the user of the device moves the device from one delivery site to another. If the delivery device is used as an inhaler type of device, this procedure is likewise applicable in order to divide the dose of medicament to be inhaled in multiple inhalation steps.

Within the meaning of substantially vertical, it is to bee understood a position wherein the medical device should be held within a conical angle of between about 0° to 150°. The maximum angle is determined by the angle of the sloping surface of the pre-treating sleeve, the weight of the obstruction means and the friction between the obstruction means and the surfaces.

With a proper design and dimensions of the components according to the present invention, it is possible to control and adjust at which angle deviation from vertical that it should no longer be possible to pre-treat the container.

It is to be understood that the embodiment described above and shown in the drawings are to be regarded as only non-limiting examples of the invention and that it can be modified within the scope of the patent claims. Thus, several parts of the described device may be replaced with other part with the same or similar function as will be readily appreciated by the skilled man.

The invention claimed is:

1. A device for delivery of medicament, comprising:
a main housing;
a multi-chamber container, comprising a first chamber containing a diluent, a second chamber containing a medicament agent, a bypass channel, an outlet provided with a mechanism to be connected to a medicament delivery member, and at least one longitudinally movable plunger;
a pre-treating arrangement acting on at least one longitudinally movable plunger for mixing the medicament agent with the diluent and obtaining a mixed medicament;
a drive force mechanism configured to act on a longitudinally movable plunger rod capable of exerting a force on the container for delivering the mixed medicament; and
an activating delivery mechanism configured to act on the drive force mechanism for initiating the delivering of medicament via the medicament delivery member;
wherein the pre-treating arrangement comprises a clickable mechanism resiliently and operably connected to a longitudinally movable second rod that is partially and slidably arranged inside the longitudinally movable plunger rod such that the clickable mechanism is adapted to be manually and intermittently activated for stepwise pushing the second rod inside the container and thereby mixing the medicament agent with the diluent.

2. The device of claim 1, wherein the clickable mechanism comprises a pre-treating sleeve and a resilient device, and the pre-treating sleeve is adapted to be manually activated from a non-depressed position to a depressed position against a counteracting force from the resilient device such that when the pre-treating sleeve is activated from the non-depressed position to the depressed position, the second rod is pushed one step inside the container and the pre-treating sleeve is restored to its non-depressed position.

3. The device of claim 2, wherein the pre-treating sleeve comprises inwardly flexible tongues arranged to interact with a ratchet having a predetermined number of steps arranged on the longitudinally movable second rod, and a last step of the ratchet is arranged for priming the container.

4. The device of claim 1, wherein the clickable mechanism comprises a delay device arranged around the clickable mechanism and configured to delay intermittent pushing of the second rod.

5. The device of claim 1, wherein the pre-treating arrangement further comprises a blocking mechanism that is operably interconnected to the clickable mechanism and that permits activation of the clickable mechanism only when the device is substantially vertical with the medicament delivery member in a specific direction.

6. The device of claim 5, wherein for an injection device, the medicament delivery member is directed upward.

7. The device of claims 5, wherein the blocking mechanism comprises a cylindrical sleeve, a cylindrical wall arranged on an inner surface of the main housing, and an obstruction device; and inner surfaces of the blocking mechanism are arranged to interact with the clickable mechanism.

8. The device of claim 7, wherein when the device is held substantially vertical, the obstruction device is an intermediate in an interaction between the blocking mechanism and the pre-treating sleeve.

9. The device of claim 1, further comprising a dose setting mechanism that is arranged to interact with the drive force mechanism and that sets a predetermined dose to be delivered.

10. The device of claim 1, wherein the activating delivery mechanism is configured to extend around the medicament delivery member upon withdrawal of the device from a delivery site.

11. The device of claim 10, wherein for injection devices, the activating delivery mechanism is configured to lockingly cover the needle after use.

12. The device of claim 1, wherein the medicament delivery member is configured as a mouth piece or a nasal piece.

13. The device of claim 1, wherein the medicament delivery member is configured as a nozzle, whereby the predetermined dose of medicament is sprayed into an eye or onto a skin of a patient.

14. The device of claim 1, wherein the medicament delivery member is configured as a member that introduces the predetermined dose of medicament to an eye of a patient as at least one drop.

15. The device of claim 1, wherein the medicament delivery member is configured as a needle for injection of the predetermined dose of medicament into a body of a patient.

* * * * *